United States Patent
Fischer et al.

(10) Patent No.: US 7,040,897 B2
(45) Date of Patent: May 9, 2006

(54) THIN, FLEXIBLE MEMBRANE DENTAL TRAYS AND SYSTEMS AND METHODS UTILIZING SUCH TRAYS

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/444,242

(22) Filed: May 23, 2003

(65) Prior Publication Data

US 2004/0234929 A1    Nov. 25, 2004

(51) Int. Cl.
*A61C 15/00*    (2006.01)

(52) U.S. Cl. ............................ 433/216; 433/37; 433/80

(58) Field of Classification Search ................. 433/37, 433/38, 45, 47, 80, 214, 215, 216
See application file for complete search history.

(56) References Cited

U.S. PATENT DOCUMENTS

| | | | |
|---|---|---|---|
| 165,584 A | 7/1875 | Hopfen | |
| 1,637,153 A | 7/1927 | Lawton | |
| 2,257,709 A | 9/1941 | Anderson | 128/260 |
| 2,835,628 A | 5/1958 | Saffir | 167/84 |
| 3,339,547 A | 9/1967 | Drabkowski | 128/260 |
| 3,527,219 A | 9/1970 | Greenberg | 128/260 |
| 3,577,640 A * | 5/1971 | Lee | 433/60 |
| 3,624,909 A | 12/1971 | Greenberg | 32/40 |
| 3,688,406 A | 9/1972 | Porter et al. | 32/40 R |
| 3,955,281 A | 5/1976 | Weitzman | 32/14 B |
| 4,044,762 A * | 8/1977 | Jacobs | 128/861 |
| 4,063,552 A * | 12/1977 | Going et al. | 128/861 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir et al. | 514/25 |
| 4,902,227 A | 2/1990 | Smith | 433/215 |
| 5,008,093 A | 4/1991 | Merianos | 423/272 |

(Continued)

FOREIGN PATENT DOCUMENTS

WO    WO 88/06869    *    9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Ralph A. Lewis
(74) *Attorney, Agent, or Firm*—Workman Nydegger (57) ABSTRACT

A dental treatment system comprises membrane treatment tray that is self-conforming to a person's own teeth when used with a sticky dental treatment composition and a support skeleton. The support skeleton maintains the flexible membrane tray in the form of tray prior to placing the tray over a person's teeth. A sticky viscous composition is either provided in or applied to the membrane tray, and then the treatment system is placed so as to position the membrane tray over the upper or lower teeth of the person. The support skeleton (internal or external) is separated from the membrane tray so that just the membrane tray remains over the person's teeth during the desired dental treatment. The sticky viscous composition holds the membrane tray against the teeth and helps it to at least partially conform to the shape of the teeth. The membrane dental tray is useful for teeth bleaching and other dental treatments known in the art.

52 Claims, 5 Drawing Sheets

U.S. PATENT DOCUMENTS

| | | | |
|---|---|---|---|
| 5,051,476 A | 9/1991 | Uji et al. | 525/186 |
| 5,085,585 A | 2/1992 | Zimble | 433/80 |
| 5,108,742 A | 4/1992 | Merianos | 424/78.32 |
| 5,112,225 A | 5/1992 | Diesso | 433/48 |
| 5,183,901 A | 2/1993 | Login et al. | 548/543 |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico et al. | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/215 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | 424/78.08 |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 * | 4/2002 | Trettenero | 433/215 |
| 6,379,147 B1 * | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 * | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | 424/49 |
| 6,682,721 B1 | 1/2004 | Kim et al. | 424/53 |
| 6,689,344 B1 | 2/2004 | Chang et al. | 424/53 |
| 6,730,316 B1 | 5/2004 | Chen | 424/435 |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Resenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagel et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

FOREIGN PATENT DOCUMENTS

| | | |
|---|---|---|
| WO | WO 03/000216 | 1/2003 |

* cited by examiner

THIN, FLEXIBLE MEMBRANE DENTAL TRAYS AND SYSTEMS AND METHODS UTILIZING SUCH TRAYS

BACKGROUND OF THE INVENTION

1. The Field of the Invention

The present invention is in the field of dental treatment systems that include trays used in applying a dental bleach, fluoride, desensitizing agent, antimicrobial agent, anticariogenic agent, or other dental agents to a person's teeth and/or gums. More particularly, the invention relates to treatment systems that include thin and flexible dental trays that are conformable to a person's teeth when used with a sticky dental treatment composition.

2. The Relevant Technology

Virtually all people desire white or whiter teeth. To achieve this goal, people either have veneers placed over their teeth or have their teeth chemically bleached. In the past, people who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a sheet of thin ethyl vinyl acetate (EVA) material, and trimming to exclude gingival coverage. This method results in a tray that is soft and flexible and that is very accurately customized to the patient's teeth. However, the method is time consuming and the resulting tray is relatively expensive.

Because of the high cost of producing custom dental trays, less costly alternatives have been developed. However, these alternatives have substantial disadvantages in terms of accuracy, effectiveness, and comfort of the finished custom tray.

One alternative is the so-called "boil and bite" tray. A relatively thick, non-custom preformed tray (similar to a mouth guard) made of EVA or polyethylene or other material is submerged in boiling water. The preformed tray is relatively thick (e.g., >2 mm) to prevent the tray from collapsing on itself and becoming entirely unusable during the heating process. Upon removal from the heated water, the tray is quickly placed inside a user's mouth. The user bites down and applies contact pressure to make an impression of the biting surfaces of the user's teeth. One problem with "boil and bite" trays is that they are relatively thick and bulky, which make them more intrusive and less comfortable to wear compared to customized trays. The thickness of large, bulky preformed trays also limits the accuracy with which they can be made to conform to the user's teeth and/or gums and makes the trays more rigid.

To the extent that boil and bite trays are made with thinner walls, such trays can be extremely difficult to work with because they tend to shrivel and collapse outside extremely narrow windows of temperature and heating time. For example, if left in a hot water bath too long (i.e., for more than a few seconds) they can quickly become limp and lose their pre-form shape, making it difficult or impossible to conform the tray to the user's teeth.

An alternative to dental trays are strips of a flexible plastic material coated with a bleaching agent that can be applied to a user's teeth. Such strips are placed against the teeth by the user to cover the labial surface of the front 6 teeth and then folded back to cover a portion of the lingual surfaces. Such dental strips can be awkward to place correctly and tend to be easily dislodged. Frequent replacement and refitting of the strips is often required. In addition, they primarily treat only the front surfaces of the teeth and provide little or no treatment of the lingual surfaces of the tooth. Moreover, they provide little or no treatment of the margins between the teeth.

Another alternative is the dual tray assembly disclosed in U.S. Pat. No. 5,616,027 to Jacobs et al. The dual tray assembly is composed of an outer tray that supports or carries an inner tray made of a thermoplastic material comprising EVA. In use, the tray assembly is submerged in hot water to render the inner tray pliable and moldable, while the outer tray remains rigid. The heated assembly is then placed in a patient's mouth to cause the inner tray to take an impression of the patient's teeth. The inner tray results in a final tray that is generally thinner and more comfortable to wear compared to conventional "boil and bite" trays that are sufficiently thick that they do not need a supporting carrier tray. Nevertheless, heating of the tray is still required, and the formed tray must typically be trimmed to yield the finished tray.

In view of the foregoing, there is an ongoing need to develop more comfortable fitting dental trays that can be easily placed over a person's teeth and that will remain in place during the desired treatment time. There is also a need to develop alternatives that are more simple to use but result in a comfortable-fitting tray in order to promote compliance with dental treatment regimes.

SUMMARY OF THE INVENTION

The present invention is directed to thin, flexible membrane dental trays that conform to the shape of a user's teeth due to the adhesive action of a sticky dental composition placed in the tray. The membrane dental trays are thin-walled, lightweight, and more comfortable than more rigid and/or thicker trays. The membrane trays are suitable for home use, and they do not require a customization step as is required with "boil and bite" trays or conventional dental office customized trays, which are vacuum formed over a stone cast derived from an impression of the person's teeth.

During manufacture and packaging of the tray, the membrane tray may optionally be filled with a sticky viscous composition (e.g., a dental bleaching composition). The membrane tray may be packaged together with an external or internal skeleton, which protects, supports, and keeps the membrane tray from collapsing and adhering to itself and/or adjacent trays that may be pre-packaged together.

In one embodiment, the membrane tray is pre-packed with an external skeleton as an assembly or treatment system. In use, the assembly is placed over the person's teeth and the external skeleton removed. Because of the extreme thinness of the tray and the presence of the sticky viscous composition, the tray is self-adhering and self-conforming (i.e., it will cling, adhere to, and readily conform to the teeth).

The membrane dental tray may optionally be available in multiple sizes to allow the selection of a size that generally conforms to the size of the person's teeth and mouth. The membrane tray may comprise any flexible polymeric material, e.g., paraffin wax; ultra low density polyethylene ("UL-DPE") and/or low density polyethylene (LDPE), either alone or blended with one or more additional polymers, e.g., ethylene-vinyl acetate copolymer ("EVA"), ε-polycaprolactone ("PCL"), other types of polyethylene ("PE"), polypropylene ("PP"), or other plastic materials; polyvinyl chloride film, or other thin polymeric materials suitable for use in making thin, flexible membrane trays. Plasticizers, flow additives, or fillers known in the art can be used as desired to modify the properties of the material used to form the membrane dental tray.

Supported by a support skeleton, the outer configuration of the membrane dental tray is preferably a horseshoe shape, with an open U-shaped cross-section having an anterior trough configured to generally fit over the upper and/or lower teeth. The walls of the membrane tray are supported in the space of the tray by the support skeleton.

The support skeleton may be semi-rigid, rigid, or flexible. Suitable materials for making the support skeleton include, for example: polyurethane, an elastomer, a molded/thermoformed plastic, closed or open cell polymeric foam, metal (e.g. stamped or formed), wire, cardboard, dissolvable materials (e.g., candy or sugar), or any other suitable materials. The support skeleton may be configured in any desired manner so as to maintain the membrane tray in a configuration that facilitates placement over a user's teeth. Because the skeleton is able to support and give form to the membrane tray, the tray itself can be extremely thin, significantly thinner than any existing trays even to the point of being collapsible absent the skeleton.

The membrane tray filled with a sticky viscous composition surrounded by the support skeleton may be pre-packaged as a kit, e.g., in a foil pouch, under a peelable cover, or in other packaging capable of keeping the composition from drying out and/or spilling. In order to use a pre-packaged tray, the user removes the tray and support skeleton assembly from the packaging and places it so that the membrane tray covers at least a portion of the user's upper or lower teeth. The support skeleton is separated from the membrane tray. Because the tray is filled with a sticky composition, once placed over the teeth, the sticky composition holds the tray against the teeth in the absence of the skeleton. An external support skeleton can be easily removed from the membrane tray once placed over the teeth to be treated, and is preferred for that reason. An internal support skeleton will either be removed prior to, or while placing the membrane tray over the teeth, or it may dissolve or disintegrate after placement.

The extreme thinness of the tray is a significant advantage over existing trays. Existing trays are thicker and less able to remain over a person's teeth unnoticed by the wearer or observer. They must typically be heated in order to make them sufficiently flexible to conform to the contour of the person's dental arch. Moreover, combining the thin membrane tray with a supporting skeleton renders such trays more easy to place over a person's teeth compared to thin dental treatment strips that have no initial form.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The invention relates to dental treatment systems that include a thin and flexible membrane dental tray and a support skeleton. The membrane dental tray readily conforms to at least a portion of a person's upper or lower teeth, such as when used in combination with a sticky dental treatment composition. The membrane dental trays are thin-walled, flexible, and more comfortable than more rigid and/or thicker dental trays known in the art. Because the membrane trays are flexible, they are supported by a support skeleton positioned adjacent to the membrane treatment tray so as to maintain the tray in the tray configuration prior to placement of the dental tray over the person's teeth. The support skeleton may be internal or external, and is typically removable. The inventive membrane trays can be used for any desired dental treatment, such as tooth bleaching, desensitizing, fluoride treatments, antimicrobial treatments, and anticariogenic treatments. Reference is now made to the drawings.

Figure 1A:
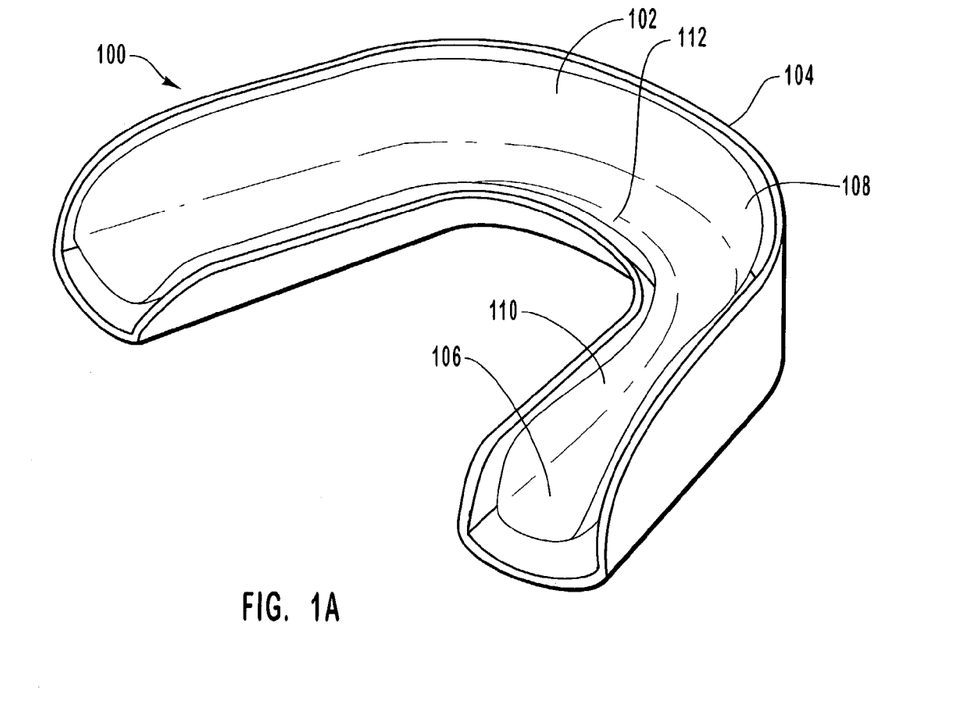
FIG. 1A is a perspective view illustrating an exemplary embodiment of a dental treatment system according to the invention comprising a membrane dental tray and external support skeleton.

FIG. 1A depicts a dental treatment system 100 that may be used in applying a treatment composition to a person's teeth. The dental treatment system 100 comprises a membrane dental treatment tray 102 and an external support skeleton 104. The membrane tray 102 is configured so as to fit over at least a portion of a person's upper or lower dental arch.

The membrane tray 102 comprises a bottom wall 106 having a generally horseshoe-shaped configuration generally conforming to the size and shape of the person's dental arch. The bottom wall 106 may be flat or curved. The membrane tray 102 further includes a front side wall 108 and a rear side wall 110 that, together with the bottom wall 106, define an interior trough having an exterior opening through which a treatment composition and the person's teeth can be inserted. The front side wall 108 extends laterally from an outer end of the bottom wall 102, while rear side wall 110 extends laterally from an inner end of bottom wall 102. The rear side wall 110 of the tray 102 may gradually open up to form an oblique angle near a middle curved portion 112 of the tray so as to better accommodate the roof of the mouth near the middle portion 112 of the tray 102. The bottom wall 106 may also have a width near the curved middle portion 112 of the tray that is advantageously less than the width of the bottom wall 106 moving from the middle portion 112 toward the ends of the tray 102. This allows for differences in the radial width of a person's incisors and canines relative to the bicuspids and molars.

The support skeleton 104 is positioned adjacent to an exterior wall of the membrane treatment tray 102 so as to maintain the tray 102 in the tray configuration prior to placement of the membrane treatment tray 102 over a person's teeth. In addition, the support skeleton 104 may help prevent the membrane treatment tray 102 from adhering to adjacent trays and/or systems when a plurality of such systems are pre-packaged together.

Figure 1B:
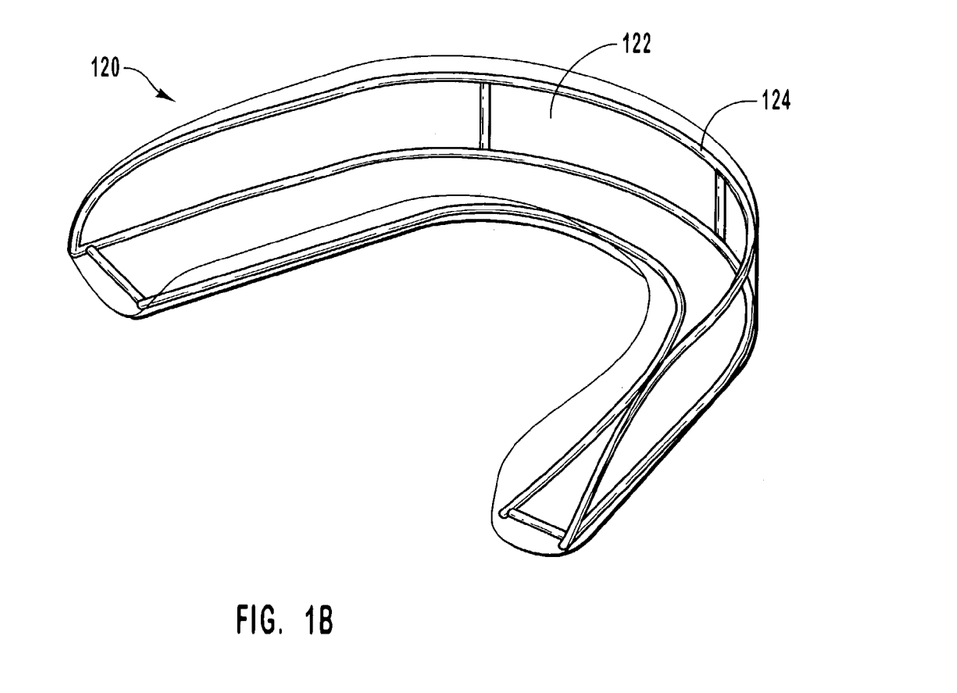
FIG. 1B is a perspective view illustrating an exemplary embodiment of a dental treatment system comprising a membrane dental tray and an internal support skeleton.

Although using an external support skeleton is preferred, an internal support skeleton may alternatively be used. FIG. 1B illustrates an alternative dental treatment system 120 comprising a membrane treatment tray 122 and internal support skeleton 124. The dental treatment system 120 is similar to the system 100 illustrated in FIG. 1A except that the support skeleton 124 is internal, positioned at least partially within the interior trough of the membrane treatment tray 122 so as to maintain the tray 122 in the tray configuration prior to placement of the membrane treatment tray over the person's teeth.

The support skeleton, whether internal or external, may be formed of polyurethane, elastomer, molded plastic, closed or open cell polymeric foam, metal, wire, cardboard, sugar, other dissolvable materials, or any other suitable material. In one particular embodiment, the internal skeleton may comprise a matrix formed of a dental treatment composition. In such an embodiment, the matrix is sufficiently rigid so as to perform the function of a skeleton, but upon wetting with water or another liquid (e.g. saliva) the matrix becomes sticky so as to hold the membrane tray against the teeth and/or gums. The matrix may be solid, semi-solid, or a firm or dry gel.

Figure 2:
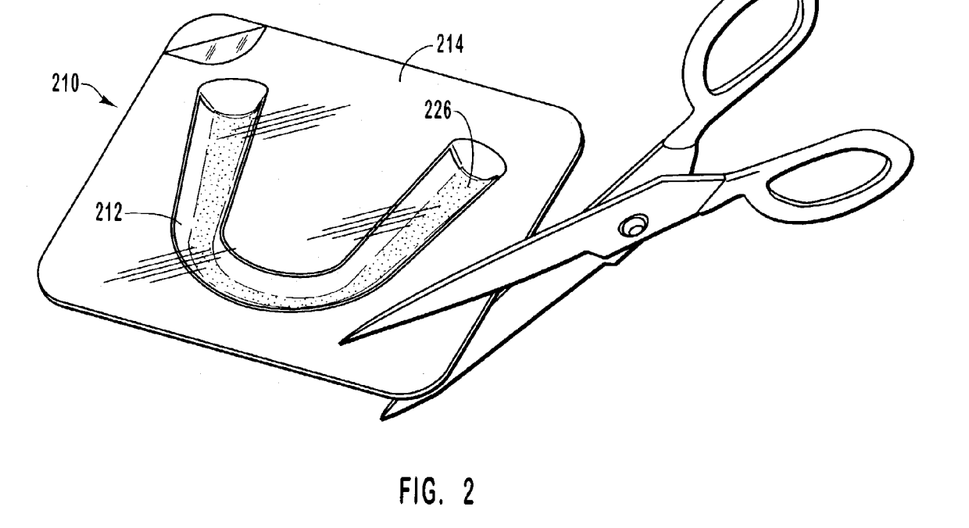
FIG. 2 is a perspective view illustrating an exemplary embodiment of a dental treatment system comprising a membrane dental tray with a dental treatment composition contained therein, and an external support skeleton formed within a flat sheet.

The dental treatment composition 232 is preferably sticky so as to adhere and retain the membrane treatment tray 212 over a person's teeth during a desired treatment time and so as to cause the tray 212 to at least partially conform to the person's teeth. As such, the dental treatment composition 232 preferably includes at least one tackifying agent that renders the treatment composition sticky and adhesive. The tackifying agent may comprise one or more of carbopol, cellulosic ether, protein, polyacrylic acid polymer, polyacrylic acid copolymer, pemulen, polyvinyl pyrrolidone, and the like.

FIG. 2 depicts an alternative dental treatment system 210 according to the invention comprising a membrane treatment tray 212 positioned within the trough of an external support skeleton 214 formed within a flat sheet 230. The sheet 230 of the dental treatment system 210 facilitates gripping of the dental treatment system 210 by a dental practitioner so as to prevent the support skeleton 214 and/or the membrane treatment tray 212 inadvertently lodging within a patient's throat (e.g., a young child or an invalid). The dental treatment system 210 is shown to include a dental treatment composition 232 placed within the interior trough of the membrane treatment tray 212. The dental treatment system 210, including the support skeleton 214 and the membrane treatment tray 212 containing a dental treatment composition 232, maybe provided within a sealed package (not shown), e.g., a plastic or foil pouch or a peelable cover. Alternatively, the dental treatment composition 232 may be placed within the interior trough of the membrane treatment tray 212 just prior to use.

Dental treatment compositions that may be used with, or as part of the dental treatment system 210, include one or more of a dental bleaching agent, an anticariogenic agent, an antimicrobial agent, a remineralizing agent, a desensitizing agent, fluoride-containing compound, and the like.

In use, dental treatment composition 232 holds the membrane treatment tray 212 to the person's teeth during treatment. In this way the treatment tray 212 and the dental treatment composition 232 work together as composition 232 holds tray 212 to the teeth, while the tray 212 provides a barrier that protects the composition 232 from saliva which might otherwise dilute and draw the composition 232 away from the tooth and/or gum surfaces to be treated.

Figure 3:
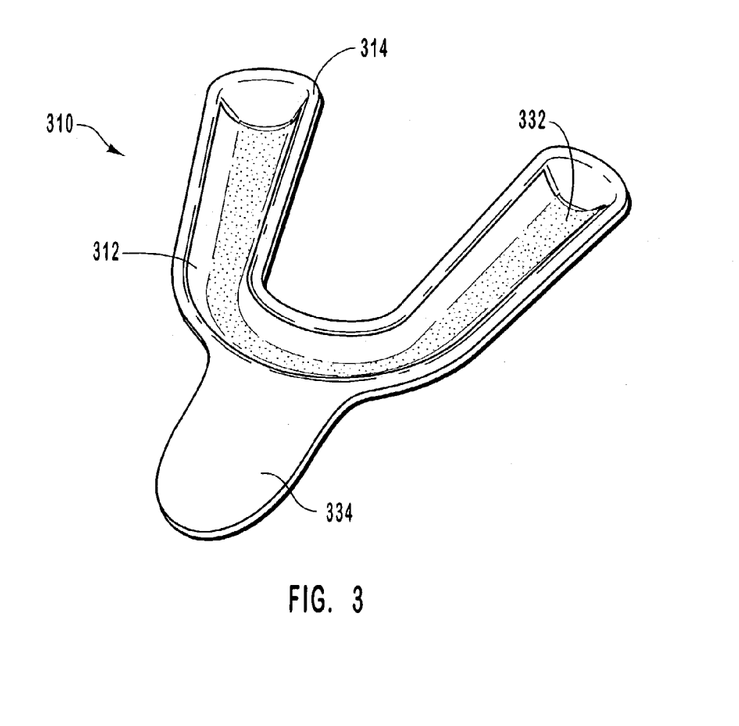
FIG. 3 is a perspective view illustrating an exemplary embodiment of a dental treatment system according to the invention comprising a membrane dental tray with a dental treatment composition contained therein, and an external support skeleton having a handle thereon.

FIG. 3 depicts another alternative dental treatment system 310 comprising a membrane treatment tray 312 filled with a dental treatment composition 332 and an external support skeleton 314 that includes a handle 334. The handle 334 facilitates placement of the membrane treatment tray 312 over a person's teeth by providing a structure that can be more easily gripped. It also facilitates easy removal of the support skeleton 314 once the membrane treatment tray 312 is adhered to the person's teeth.

Figure 4:
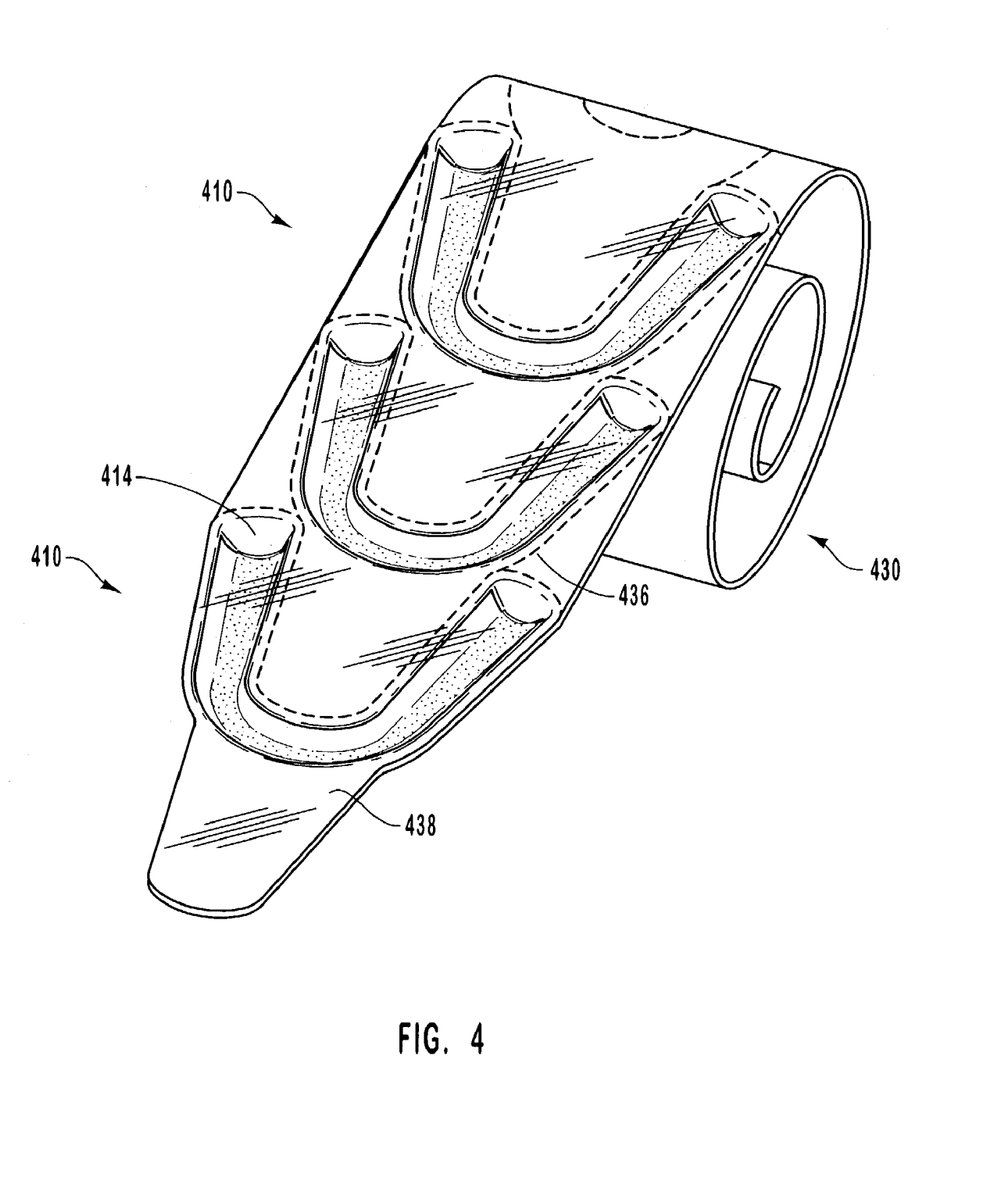
FIG. 4 is a perspective view illustrating a plurality of pre-packaged dental treatment systems according to the invention that are initially connected together as a roll.

The dental treatment systems according to the invention may be provided in a kit including a plurality of membrane treatment trays and support skeletons. When formed of a flexible material, the dental treatment system kit may be packaged in a roll. Referring to FIG. 4, attachment of the dental treatment systems 410 in a roll 430 may be accomplished by providing a continuous sheet and forming individual support skeletons 414 from the sheet that can be detached from the sheet as desired. For a support skeleton that includes a handle (similar to that illustrated in FIG. 3), the handle 434 attached to a first support skeleton 414 may be disposed within the space defined by the horseshoe shaped support skeleton 414 of an adjacent treatment system 410. By packaging the dental treatment systems in a roll, a single dental treatment system can be detached from the roll for use. The interfaces between individual treatment systems 410 may include perforations 436 that make it easier to remove a single system from the roll. In addition, each individual system may optionally be packaged under a peelable cover 438 to keep the sticky viscous composition from drying out.

The membrane treatment trays can be made of any appropriate material that is sufficiently flexible so as to at least partially conform to a person's teeth at ambient temperatures. Preferred materials include at least one of ultra low density polyethylene (ULDPE), low density polyethylene, paraffin wax, ethylene-vinyl acetate (EVA) copolymer, polycaprolactone (PCL), polyethylene, polypropylene, or polyvinyl chloride (PVC). Flow additives, plasticizers, and fillers may be added as desired.

Examples of suitable ULDPE materials include various polymers sold under the general trade name Attane® by Dow Chemical. Another suitable ULDPE material is Exact® 4041 made by Exxon-Mobil Chemical. An example of a suitable EVA material is Elvax® 250, available from Dupont. An example of a suitable PCL material is Capra® 650 from Solvoy-Interox. Other materials and blends used in making dental trays are disclosed in U.S. Pat. No. 5,769,633 to Jacobs et al., U.S. Pat. No. 5,051,476 to Uji et al., and U.S. Pat. No. 6,089,869 to Schwartz. For purposes of disclosing materials that can be made into membrane treatment trays, the foregoing patents are incorporated herein by reference.

In order to maximize comfort and also to yield a membrane tray that is able to readily conform to a person's teeth when in use, the membrane treatment tray preferably has a wall thickness in a range of about 0.0001 inch to about 0.01 inch, more preferably in a range of about 0.0005 inch to about 0.005 inch, and most preferably in a range of about 0.0001 inch to about 0.003 inch.

The membrane treatment tray may be transparent, allowing the dental practitioner and others to easily see the level and position of the dental treatment composition, or alternatively, the treatment tray may be brightly colored so as to facilitate easy and quick identification while in use. These examples are meant to be illustrative, and of course it is within the scope of the invention to use various other colors and configurations.

The treatment tray of the present invention is designed to be disposed of after a single use. The trays are far less expensive compared to customized dental trays, which allows the membrane treatment trays to be disposable. Preferably, a new treatment tray is used for each treatment, although it is within the scope of the invention to clean the tray for reuse.

The treatment trays are suitable for home use, and they do not require a customization step as required with "boil and bite" trays or dental office customized trays. Other advantages of using a membrane treatment tray include an increase in comfort because the treatment tray is significantly thinner than existing trays, and the tray also provides excellent conformation to the teeth, which results in better treatment results when compared to, for example, non-customized bleaching strips.

Exemplary dental treatment compositions that are sticky and viscous are disclosed in U.S. Pat. No. 5,376,006 to Fischer, U.S. Pat. No. 5,851,512 to Fischer et al., U.S. Pat. No. 5,985,249 to Fischer, U.S. Pat. No. 6,309,625, to Jensen et al., and U.S. Pat. No. 6,312,671 to Jensen et al. For purposes of disclosing dental treatment compositions that are sufficiently sticky so as to retain and adhere a membrane treatment tray according to the invention over a person's teeth in a manner so that the membrane treatment tray at least partially conforms to the person's teeth, the foregoing patents are incorporated by reference.

Figure 5:
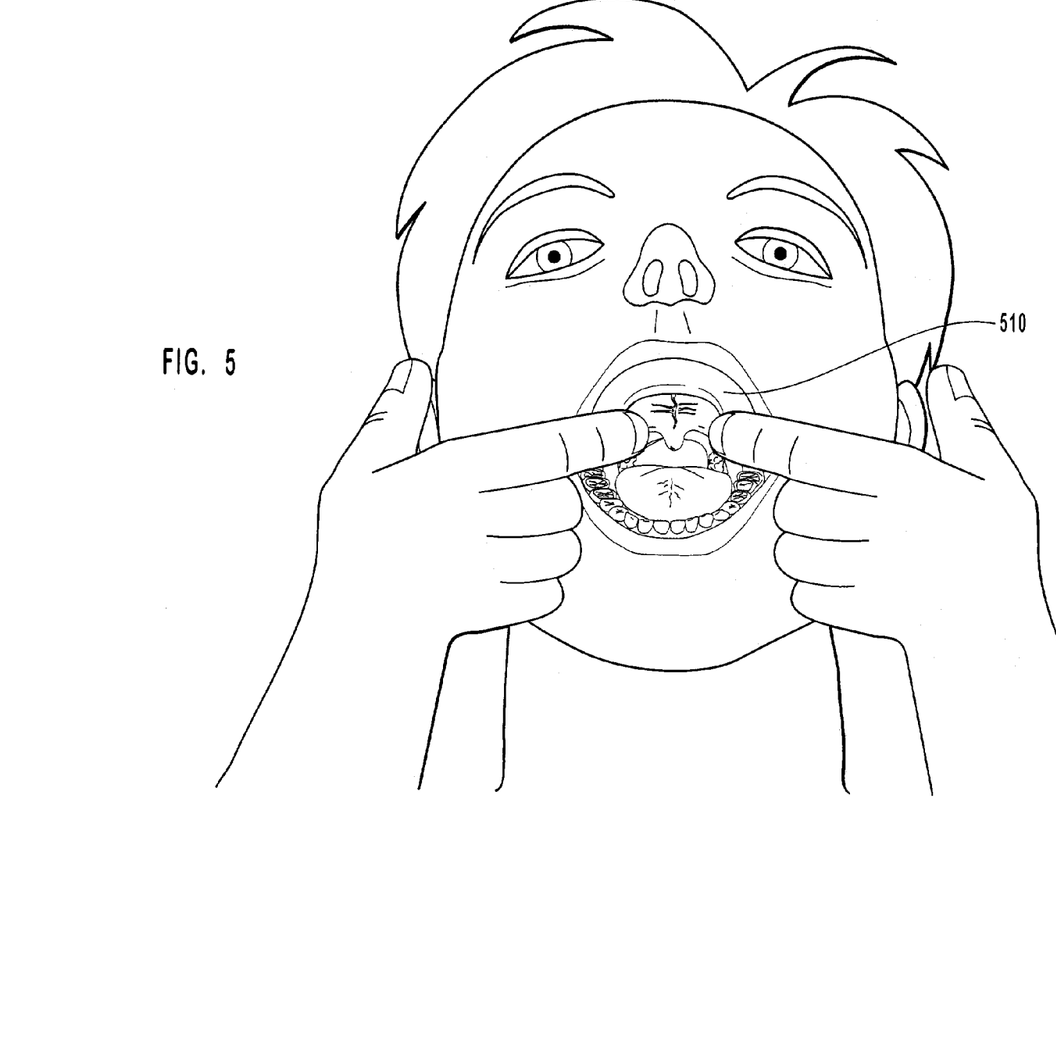
FIG. 5 illustrates a membrane dental tray with an attached external support skeleton being placed over a person's teeth.

FIG. 5 depicts a person placing a dental treatment system 510 comprising a membrane treatment tray containing a dental treatment composition and a support skeleton over the person's teeth. The support skeleton (e.g., external support skeleton) maintains a gentle treatment tray in a desired configuration so as to facilitate placement of the tray over the person's teeth. The support skeleton provides an advantage over flexible dental treatment strips that must be placed over and wrapped around the occlusal edges of a person's teeth without the assistance of a support skeleton. Once the flexible membrane treatment tray has been placed over the person's teeth, the external support skeleton is removed so that only the membrane treatment tray containing the treatment composition remains over the person's teeth.

Figure 6:
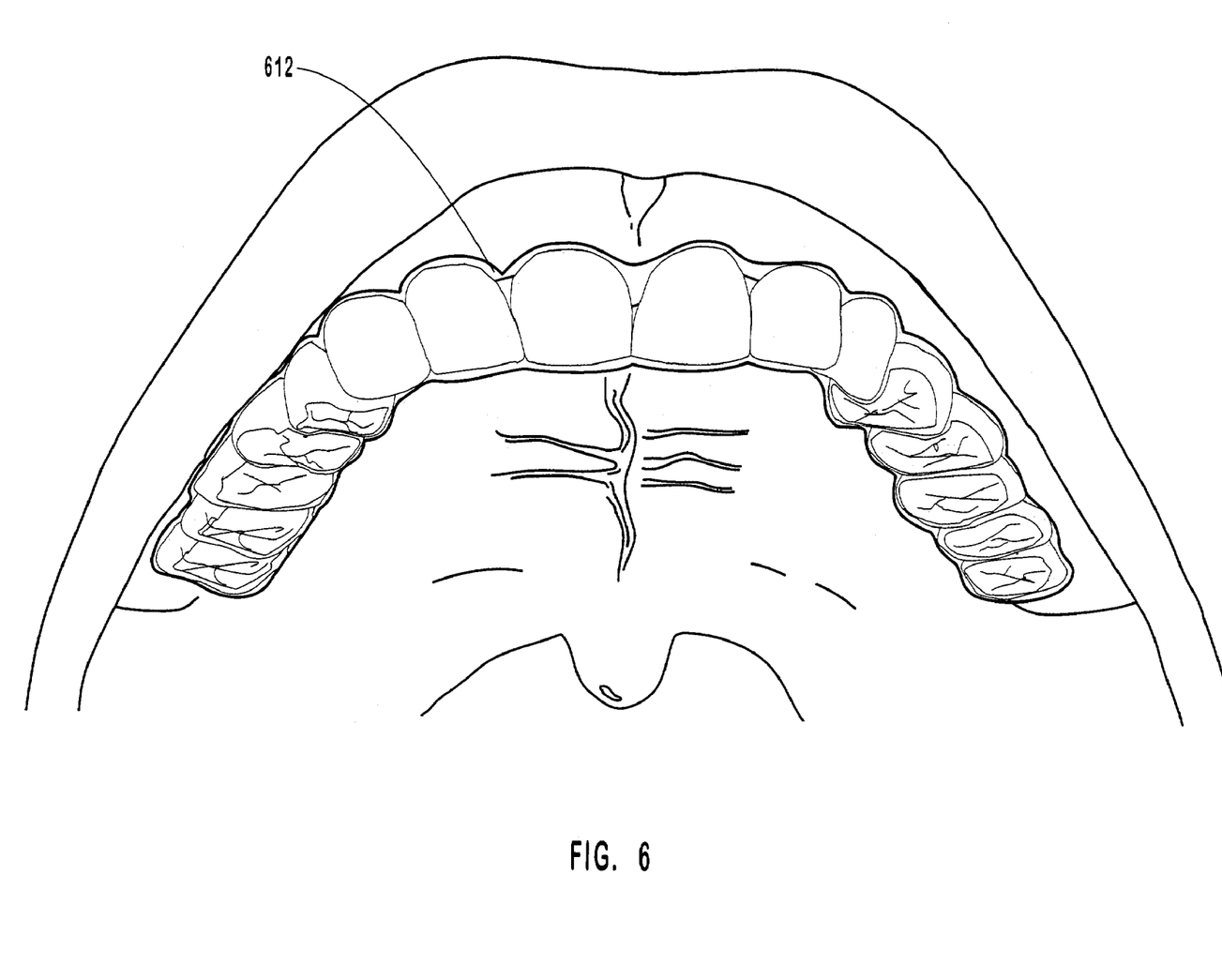
FIG. 6 illustrates a membrane dental tray after it has been placed over a person's teeth and caused to conform to the person's teeth as a result of the adhesive action of a sticky dental treatment composition within the tray.

FIG. 6 illustrates how a membrane treatment tray according to the invention is able to at least partially conform to a person's teeth due to adhesive action of a sticky dental treatment composition. Although it is certainly within the scope of the invention to utilize dental treatment compositions that are less sticky (or even non-sticky) it is preferable for the treatment composition to be sticky in order to adhere and retain the membrane treatment tray over the person's teeth during a desired dental treatment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental treatment system for use in applying a treatment composition to a person's teeth, comprising:

a dental treatment tray that is adapted to be worn without requiring customization, the dental treatment tray having a tray configuration that is adapted to permit the treatment tray to fit and be worn over at least a portion of a person's upper or lower dental arch when the tray is used to apply a treatment composition, the treatment tray comprising a thin-walled, flexible membrane material that is adapted to at least partially conform to the person's teeth when worn by a patient so as to be used to apply a dental treatment composition;

a support skeleton positioned adjacent to the dental treatment tray so as to maintain the thin-walled flexible membrane material tray in the configuration of a tray prior to its placement over the person's teeth; and when maintained in the configuration of a tray by the support skeleton, the thin-walled flexible membrane defining an interior trough for holding the dental treatment composition, and having an exterior opening through which the person's teeth can be inserted.

2. A dental treatment system as recited in claim 1, wherein the interior trough further includes a dental treatment composition contained therein.

3. A dental treatment system as recited in claim 2, wherein the dental treatment composition is sticky so as to adhere and retain the dental treatment tray over a person's teeth during a desired treatment time and so as to cause the tray to at least partially conform to the person's teeth.

4. A dental treatment system as recited in claim 2, wherein the dental treatment composition comprises at least one tackifying agent.

5. A dental treatment system for use in applying a treatment composition to a person's teeth, comprising:

a dental treatment tray having a tray configuration so as to fit over at least a portion of a person's upper or lower dental arch, the treatment tray having a thickness and flexibility so that it at least partially conforms to the person's teeth when used in combination with a sticky dental treatment composition, the treatment tray defining an interior trough having an exterior opening through which a treatment composition and the person's teeth can be inserted;

a support skeleton positioned adjacent to the dental treatment tray so as to maintain the tray in the tray configuration prior to placement of the dental treatment tray over the person's teeth; and wherein the interior trough further includes a dental treatment composition contained therein that comprises at least one tackifying agent.

6. A dental treatment system as recited in claim 4 or 5, wherein the tackifying agent comprises at least one of carbopol, cellulosic ether, protein, polyacrylic acid polymer, polyacrylic acid copolymer, pemulen, or polyvinyl pyrrolidone.

7. A dental treatment system as recited in claim 2 or 5, wherein the dental treatment composition comprises at least one of a dental bleaching agent, an anticariogenic agent, an antimicrobial agent, a remineralizing agent, a desensitizing agent, or fluoride.

8. A dental treatment system as recited in claim 2 or 5, wherein the support skeleton and dental treatment tray containing the dental treatment composition are contained within a sealed package.

9. A dental treatment system as recited in claim 8, wherein the sealed package comprises at least one of a plastic or foil pouch.

10. A dental treatment system as recited in claim 8, wherein the sealed package comprises a peelable cover.

11. A dental treatment system as recited in claim 1 or 5, wherein the dental treatment tray comprises at least one of ultra low density polyethylene, low density polyethylene, paraflin wax, ethylene-vinyl acetate copolymer, polycaprolactone, polyethylene, or polypropylene.

12. A dental treatment system as recited in claim 1 or 5, wherein the dental treatment tray has a wall thickness in a range of about 0.0001 inch to about 0.01 inch.

13. A dental treatment system as recited in claim 1 or 5, wherein the dental treatment tray has a wall thickness in a range of about 0.001 inch to about 0.005 inch.

14. A dental treatment system as recited in claim 1 or 5, wherein the dental treatment tray has a wall thickness in a range or about 0.0025 inch to about 0.003 inch.

15. A dental treatment system as recited in claim 1 or 5, wherein the dental treatment tray is sufficiently thin and flexible that it does not maintain its physical integrity as a tray when separated from the support skeleton absent external support.

16. A dental treatment system as recited in claim l or 5, wherein the dental treatment tray is sufficiently thin and flexible that it does not maintain its physical integrity as a tray when removed from a person's teeth absent external support.

17. A dental treatment system as recited in claim 1 or 5, wherein the support skeleton is an external skeleton positioned at least partially adjacent to an exterior wall of the dental treatment tray.

18. A dental treatment system as recited in claim 1 or 5, wherein the support skeleton is an internal skeleton positioned at least partially within the interior trough of the dental treatment tray.

19. A dental treatment system as recited in claim 1 or 5, wherein the support skeleton comprises a handle that facilitates placement of the dental treatment tray over a person's teeth.

20. A dental treatment system as recited in claim 1 or 5, wherein the support skeleton comprises at least one of polyurethane, elastomer, molded plastic, closed or open cell polymeric foam, metal, wire, cardboard, or sugar.

21. A dental treatment system as recited in claim 18, wherein the internal skeleton comprises a sufficiently rigid treatment matrix, which upon wetting becomes sufficiently sticky to hold the dental treatment tray against the teeth and/or gums.

22. A dental treatment system as recited in claims 1 or 5, comprising a plurality of dental treatment trays and support skeletons within a kit.

23. A dental treatment system as recited in claim 21, wherein the plurality of dental treatment trays and support skeletons are packaged together in a roll.

24. A dental treatment kit for use in applying a treatment composition to a person's teeth, comprising:

a dental treatment tray that is adapted to be worn without requiring customization, the dental treatment tray having a tray configuration that is adapted to permit the treatment tray to fit and be worn over at least a portion of a person's upper or lower dental arch when the tray is used to apply treatment composition, the treatment tray comprising a thin-walled, flexible membrane material that is adapted to at least partially conform to the person's teeth when worn by a patient so as to be used to apply a dental treatment composition, the treatment tray defining an interior trough for holding the dental treatment composition, and having an exterior opening through which the person's teeth can be inserted;

a support skeleton positioned adjacent to the dental treatment tray so as to maintain the thin-walled flexible membrane material tray in the configuration of a tray prior to its placement of the dental over the person's teeth; and a dental treatment composition for treating the patient's teeth when placed in the tray that is worn by the patient.

25. A dental treatment kit as recited in claim 24, wherein the dental treatment tray comprises at least one of ultra low density polyethylene, low density polyethylene, paraffin wax, ethylene-vinyl acetate copolymer, polycaprolactone, polyethylene, or polypropylene.

26. A dental treatment kit as recited in claim 24, wherein the dental treatment tray has a wall thickness in a range of about 0.0001 inch to about 0.01 inch.

27. A dental treatment kit as recited in claim 24, wherein the dental treatment tray has a wall thickness in a range of about 0.001 inch to about 0.005 inch.

28. A dental treatment kit as recited in claim 24, wherein the dental treatment tray has a wall thickness in a range of about 0.0025 inch to about 0.003 inch.

29. A dental treatment kit as recited in claim 24, wherein the dental treatment tray is sufficiently thin and flexible that it does not maintain its physical integrity as a tray when separated from the support skeleton absent external support.

30. A dental treatment kit as recited in claim 24, wherein the dental treatment tray is sufficiently thin and flexible that it does not maintain its physical integrity as a tray when removed from a person's teeth absent external support.

31. A dental treatment kit as recited in claim 24, wherein the support skeleton is an external skeleton positioned at least partially adjacent to an exterior wall of the dental treatment tray.

32. A dental treatment kit as recited in claim 24, wherein the support skeleton is an internal skeleton positioned at least partially within the interior trough or the dental treatment tray.

33. A dental treatment kit as recited in claim 32, wherein the internal skeleton comprises a sufficiently rigid treatment matrix, which upon wetting becomes sufficiently sticky to hold the dental treatment tray against the teeth and/or gums.

34. A dental treatment kit as recited in claim 24, wherein the support skeleton comprises a handle that facilitates placement of the dental treatment tray over a person's teeth.

35. A dental treatment kit as recited in claim 24, wherein the support skeleton comprises at least one of polyurethane, elastomer, molded plastic, closed or open cell polymeric foam, metal, wire, cardboard, or sugar.

36. A dental treatment kit as recited in claim 24, comprising a plurality of dental treatment trays and support skeletons.

37. A dental treatment kit as recited in claim 36, wherein the plurality of dental treatment trays and support skeletons are packaged together in a roll.

38. A method of applying a treatment composition to a person's teeth, comprising:

(a) providing a dental treatment system comprising:
  a dental treatment tray that is adapted to be worn without requiring customization, the dental treatment tray having a tray configuration so as that is adapted to permit the treatment tray to fit and be worn over at least a portion of a person's upper or lower dental arch when the tray is used to apply a treatment composition, the treatment tray comprising a thin-walled, flexible membrane material that is adapted to at least partially conforms to the person's teeth when worn by a patient so as to be used to apply a dental treatment composition, the treatment tray defining an interior trough for holding the dental treatment composition, and having an exterior opening through which the person's teeth can be inserted; and
  a support skeleton positioned adjacent to the dental treatment tray so as to maintain the thin-walled flexible membrane material in the configuration of a tray prior to its placement over the person's teeth; and
  when maintained in the configuration of a tray by the support skeleton, the thin-walled flexible membrane defining an interior trough for holding the dental treatment composition, and having an exterior opening through which the person's teeth can be inserted;
(b) introducing a quantity of a dental treatment composition into the interior trough of the dental treatment tray;
(c) placing the dental treatment tray over at least a portion of the person's teeth;
(d) separating the support skeleton from the dental treatment tray; and
(e) at least partially conforming the thin-walled flexible membrane and the treatment composition contained therein over the patient's teeth and then wearing the dental treatment tray for a period of time to permit treatment of the teeth by the dental composition.

39. A method as recited in claim 38, wherein the dental treatment composition is sticky so that it helps to partially conform the treatment tray to the patient's teeth, and adheres and retains the dental treatment tray over the person's teeth during a desired treatment time.

40. A dental treatment kit as recited in claim 24, wherein the interior trough further includes a dental treatment composition contained therein.

41. A dental treatment kit as recited in claim 40, wherein the dental treatment composition is sticky so as to adhere and retain the dental treatment tray over a person's teeth during a desired treatment time and so as to cause the tray to at least partially conform to the person's teeth.

42. A dental treatment kit as recited in claim 40, wherein the dental treatment composition comprises at least one tackifying agent.

43. A dental treatment kit as recited in claim 42, wherein the tackifying agent comprises at least one of carbopol, cellulosic ether, protein, polyacrylic acid polymer, polyacrylic acid copolymer, pemulen, or polyvinyl pyrrolidone.

44. A dental treatment kit as recited in claim 40, wherein the dental treatment composition comprises at least one of a dental bleaching agent, an anticariogenic agent, an antimicrobial agent, a remineralizing agent, a desensitizing agent, or fluoride.

45. A dental treatment kit as recited in claim 40, wherein the support skeleton and dental treatment tray containing the dental treatment composition are contained within a sealed package.

46. A dental treatment kit as recited in claim 45, wherein the sealed package comprises at least one of a plastic or foil pouch.

47. A dental treatment kit as recited in claim 45, wherein the sealed package comprises a peelable cover.

48. A method of applying a treatment composition to a person's teeth, comprising:
  (a) providing a dental treatment system comprising:
    a dental treatment tray having a tray configuration so as to fit over at least a portion of a person's upper or lower dental arch, the treatment tray having a thickness and flexibility so that it at least partially conforms to the person's teeth when used in combination with a sticky dental treatment composition, the treatment tray defining an interior trough having an exterior opening through which a treatment composition and the person's teeth can be inserted; and
    a support skeleton positioned adjacent to the dental treatment tray so as to maintain the tray in the tray configuration prior to placement of the dental treatment tray over the person's teeth;
  (b) introducing a quantity of a dental treatment composition into the interior trough of the dental treatment tray, the dental treatment composition comprising at least one tackifying agent;
  (c) placing the dental treatment tray over at least a portion of the person's teeth; and
  (d) separating the support skeleton from the dental treatment tray.

49. A method as recited in claims 38 or 48, wherein the support skeleton is an external skeleton initially positioned at least partially adjacent to an exterior wall of the dental treatment tray such that (d) is performed subsequent to (c).

50. A method as recited in claims 38 or 48, wherein the support skeleton is an internal skeleton positioned at least partially within the interior trough of the dental treatment tray such that (d) is performed prior to or substantially simultaneously with (c).

51. A dental treatment system for use in applying a treatment composition to a person's teeth, comprising:
  a dental treatment tray having a tray configuration so as to fit over at least a portion of a person's upper or lower dental arch, the treatment tray having a thickness and flexibility so that it at least partially conforms to the person's teeth when used in combination with a sticky dental treatment composition, the treatment tray defining an interior trough having an exterior opening through which a treatment composition and the person's teeth can be inserted;
  a support skeleton positioned adjacent to the dental treatment tray so as to maintain the tray in the tray configuration prior to placement of the dental treatment tray over the person's teeth; and
  wherein the support skeleton is an internal skeleton positioned at least partially within the interior trough of the dental treatment tray.

52. A method of applying a treatment composition to a person's teeth, comprising:
  (a) providing a dental treatment system comprising:
    a dental treatment tray having a tray configuration so as to fit over at least a portion of a person's upper or lower dental arch, the treatment tray having a thickness and flexibility so that it at least partially conforms to the person's teeth when used in combination with a sticky dental treatment composition, the treatment tray defining an interior trough having an exterior opening through which a treatment composition and the person's teeth can be inserted; and a support skeleton positioned adjacent to the dental treatment tray so as to maintain the tray in the tray configuration prior to placement of the dental treatment tray over the person's teeth, and wherein the support skeleton is an internal skeleton positioned at least partially within the interior trough of the dental treatment tray such that (d) is performed prior to or substantially simultaneously with (c);

(b) introducing a quantity of a dental treatment composition into the interior trough of the dental treatment tray;

(c) placing the dental treatment tray over at least a portion of the person's teeth; and (d) separating the support skeleton from the dental treatment tray.

* * * * *